US006750346B2

(12) United States Patent
Czerney et al.

(10) Patent No.: US 6,750,346 B2

(45) Date of Patent: Jun. 15, 2004

(54) STABLE NEAR-INFRARED (NIR) MARKER DYES BASED ON BENZOPYRYLIUM-POLYMETHINES

(75) Inventors: Peter Czerney, Weimar (DE); Frank Lehmann, Jena (DE); Bernd Schweder, Jena (DE); Matthias Wenzel, Jena (DE)

(73) Assignee: Carl Zeiss Jena GmbH, Jena (DE)

( * ) Notice: Subject to any disclaimer, the term of this patent is extended or adjusted under 35 U.S.C. 154(b) by 0 days.

(21) Appl. No.: 10/031,741

(22) PCT Filed: May 22, 2001

(86) PCT No.: PCT/DE01/01946

§ 371 (c)(1),
(2), (4) Date: Jan. 22, 2002

(87) PCT Pub. No.: WO01/90253

PCT Pub. Date: Nov. 29, 2001

(65) Prior Publication Data

US 2002/0115862 A1 Aug. 22, 2002

(30) Foreign Application Priority Data

May 23, 2000 (DE) ........................................ 100 25 820
May 23, 2000 (DE) .................................... 200 22 277 U

(51) Int. Cl.$^{7}$ .................... C07D 513/00; C07D 498/00; C07D 421/00; C07D 735/04

(52) U.S. Cl. ............................ 546/66; 546/89; 546/99; 546/268.1; 548/159; 548/213; 548/305.1; 549/23; 549/24; 549/404

(58) Field of Search ................................ 546/268.1, 66, 546/89, 99; 548/159, 217, 305.1; 549/23, 24, 404; 430/332

(56) References Cited

U.S. PATENT DOCUMENTS 3,567,438 A 3/1971 Brooker et al.

FOREIGN PATENT DOCUMENTS

| | | |
|---|---|---|
| DE | 43 41 618 | 6/1995 |
| JP | 63-136054 | 6/1988 |
| JP | 63-141068 | 6/1988 |

OTHER PUBLICATIONS

Okada et al. Chemical Abstracts, vol. 108 No. 195610, "Mehyne laser dyes", (1988).*

Czermey et al, Chemical Abstracts, vol. 138 No. 74710, "2– or 4–Chromenylidene–based merocyanines and their use as florescent marker dyes"., (2003).*

* cited by examiner

*Primary Examiner*—Raymond Covington
(74) *Attorney, Agent, or Firm*—Reed Smith LLP

(57) ABSTRACT

The disclosure is directed to so-called laser-compatible NIR marker dyes based on polymethines for use in optical, in particular, fluorescence optical determination and detection methods, for example, in the fields of medicine, pharmaceutics and in the areas of life science, materials science and environmental science. The disclosure further discusses the aim of the invention which was to create NIR marker dyes based on polymethine which have a high degree of photostability and stability in storage as well as a high fluorescent yield and which can be excited to fluorescence in the easiest possible manner by means of laser radiation in the visible or NIR spectral range, particularly with light of an argon, helium/neon, or diode laser. Dyes based on polymethine of general formula (I) are used.

8 Claims, 3 Drawing Sheets

O

N

O i) $CH_3MgBr$
ii) HCl / $HBF_4$ $CH_3$

N

O $BF_4$

2b $(C_2H_5O)_3CH$/pyridine

STABLE NEAR-INFRARED (NIR) MARKER DYES BASED ON BENZOPYRYLIUM-POLYMETHINES

CROSS-REFERENCE TO RELATED APPLICATIONS

This application claims priority of International Application No. PCT/DE01/01946, filed May 22, 2001 and German Application No. 100 25 820.4, filed May 23, 2000 and No. 200 22 277.5, filed May 23, 2000, the complete disclosures of which are hereby incorporated by reference.

BACKGROUND OF THE INVENTION a) Field of the Invention

The invention is directed to so-called laser-compatible NIR marker dyes based on polymethines for use in optical, in particular, fluorescence optical determination and detection methods. Typical applications of the process are based on the reaction of dye marked antigens, antibodies, ligands or DNA segments with the respective complementary species.

Possible uses exist, for example, in the fields of medicine, pharmaceutics and in the areas of life science, materials science, in environmental monitoring and in the detection of organic and inorganic micro-samples occurring naturally and in technological contexts, but they are not limited to the aforementioned fields.

b) Description of the Related Art

The usability of polymethines as NIR markers has been known of for a long time; they distinguish themselves by their strong absorption maxima which can easily be transposed into the NIR range (Fabian, J.; Nakazumi, H.; Matsuoka, M.: Chem. Rev. 1992, 92, 1197). With a suitable substituent pattern and pi-electron system and at a sufficient quantum yield they also fluoresce in the red and near infrared (NIR) range. Correspondingly, these compounds are widely used in different technological fields: as sensitizers in AgX materials, as laser dyes, as quantum counters, as indicator dyes in sensor technology, as light absorbers in writable CDs and last but not least as biomarkers ("Near-Infrared Dyes for High Technology Application", published by Daehne, S.; Resch-Genger, U.; Wolfbeis, O.-S., Kluwer, Academic Publishers—Dordrecht/Boston/London—1998).

The number of polymethines used as biomarkers is limited. So far, only the trimethine Cy3 derived from astraphloxine (DE 410 487), the vinylogous pentamethine Cy5 and the doubly vinylogous heptamethine Cy7 with absorption maxima at approximately 550 nm, approximately 650 nm and approximately 750 nm have so far found wide commercial application in this manner (U.S. Pat. No. 5,627,027). Also available are the polysulfonated trimethine Cy3.5 derived from the commercial hepatmethine "Indocyaninegreen" or "Cardio Green" and the pentamethine Cy5.5 (U.S. Pat. No. 5,569,766). Heptamethines with aliphatic bridges in the polymethine chain have been developed by Patonay (U.S. Pat. No. 5,800,995). All commercial biomarkers are characterized by terminal heteroaromatics derived from indene or heteroindene (Fischer's base). If methylsubstituted cycloimmonium salts are used as terminal polymethine building blocks, it is necessary to arrange at least five sequential $sp^2$ hybridized carbon atoms (pentamethines) between the heterocycles to generate absorption maxima at the boundary to the NIR range.

The NIR polymethines used in technology as biomarkers have the distinct disadvantage that lengthening the polymethine chain increases the opportunities for nucleophilic or electrophilic attack on the chain, in consequence of which the pi-system is destroyed. Further disadvantages of these marker dyes consist in their insufficient photostability and stability in storage, complicated synthesis and purification stages, low absorption coefficients/low fluorescent quantum yields as well as undesired changes of their optical properties in the presence of or after bonding with proteins or nucleic acid oligomeres. For example, a reduction of the fluorescent quantum yield of Cy5 has been described for the covalent bonding with different albumins (Oswald, B.; Patsenker, L.; Duschl, J.; Szmacinski, H.; Wolfbeis, O. S.; Terpeschnig, E.; Bioconjugate Chem. 1999, 10, 925–931).

The use of pyrylium and benzopyrylium heterocycles or the corresponding mesomeric chromenes as terminal end groups in marker dyes in biologically relevant systems is so far not known in the art. This is due to the extreme sensitivity to hydrolysis of these pi-deficient aromatics, especially in an aqueous basic environment (H. Lietz, G. Haucke, P. Czerney, B. John, J. Prakt. Chem., 1996, 338, 725–730).

Telfer et al. (U.S. Pat. No. 5,262,549) describe symmetrical trimethines based on 2-alkyl substituted benzopyrylium salts for the use as NIR absorbers in polimeric media with a reduced tendency towards aggregation in these media.

OBJECT AND SUMMARY OF THE INVENTION

The primary object of the invention is to create NIR marker dyes based on polymethine which have a high degree of photostability and stability in storage as well as a high fluorescent yield and which can be excited to fluorescence in the easiest possible manner by means of laser radiation in the longwave visible or NIR spectral range, particularly with light of a helium/neon or diode laser.

The present invention describes marker dyes based on non-symmetrical polymethines which contain a substituted ω-(benz[b]pyran-4-ylidene)alk-1-enyl) unit of general formula (I),

I

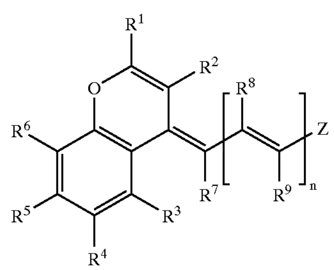

where Z is a substituted derivative of benzooxazol, benzothiazol, 2,3,3-trimethylindolenine, 2,3,3-trimethyl-4,5-benzo3H-indolenine, 3- and 4-picoline, lepidine, chinaldine and 9-methylacridine derivatives with the general formulae IIa or IIb or IIc IIa IIb IIc

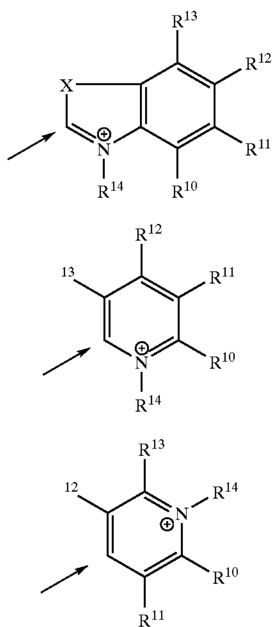

and where

X stands for an element of the group O, S, Se or the structural element N-alkyl or $C(alkyl)_2$, N stands for the numerical value 1, 2 or 3, $R^1$–$R^{14}$ are equal or different and can be hydrogen, one or more alkyl, aryl, heteroaryl or heterocycloaliphathic fragments, a hydroxy or alkoxy group, an alkylsubstituted or cyclical amine function and/or two fragments in ortho position to each other, for example $R^{10}$ and $R^{11}$, can together form another aromatic ring, At least one of the substituents $R^1$–$R^{14}$ can be a solubilizing or ionizable or ionized substituent, like cyclodextrine, sugar, $SO_3^-$, $PO_3^{2-}$, $COO^-$, or $NR_3^+$, which determines the hydrophilic properties of these dyes; here it is possible that this substituent can be bound to the marker dye by means of a spacer group, At least one of the substituents $R^1$–$R^{14}$ can stand for a reactive group which facilitates a covalent linking of the dye to the aforementioned carrier molecules, while this substituent can also be bound to the dye by means of a spacer group, and $R^1$ is a substituent which has a quarternary C-atom in alpha-position relative to the pyran ring. Examples for such substituents are t-butyl (—$C(CH_3)_3$) and adamantyl (—$C_{10}H_{15}$/tricyclo[$3.3.1.1^{3,7}$]decyl).

Subclaims 2 to 20 list specific embodiment forms and applications of the marker dyes.

These substituted derivatives of indol, heteroindol, pyridine, chinoline or acridine of the general formula I can be used as dyes for the optical marking of organic or inorganic microparticles, for example of proteins, nucleic acids, DNA, sugars, biological cells, lipids, drugs or organic or inorganic polymeric carrier substances.

Here, the marking of particles can be done by the formation of ionic interaction between the markers of general formula I and the substances to be marked.

The functional groups of these markers activated with regards to nucleophiles can couple covalently with an OH, $NH_2$ or SH function, which therefore creates a system for the qualitative and quantitative determination of organic and inorganic substances, like said proteins, nucleic acids, DNA, sugars, biological cells, lipids, drugs or organic or inorganic polymers.

The coupling reaction can take place in an aqueous or mostly aqueous solution, preferably at room temperature. During this a conjugate with fluorescent properties is created.

By means of the preparation of non-symmetrical polymethines, which on the one hand have an easily derivatizable heterocycle of the type of the pyridine, chinoline, indol, heteroindol or acridine derivatives and on the other hand have a novel 6-ring heterocycle, in particular the following advantages are achieved:

Trimethines already absorb in the spectral range >650 nm and have a significantly improved photochemical and thermal stability when compared with polymethines known so far in the art which have absorption maxima >650 nm (penta- and heptamethines).

By means of molecular engineering, it is possible to control the position and intensity of the absorption and emission maxima at will and to adapt them to emission wavelengths of different excitation lasers, in particular NIR laser diodes.

The marker dyes can be produced by a relatively simple two-stage synthesis with which a variety of dyes with functionalities that differ, for example, with regards to the total charge of the dye and the number, specificity and reactivity of the activated group used for the immobilization can be provided in a manner that is specific to the respective application.

Compounds with the general formula I as well as systems derived from them (conjugates) can be used in optical, in particular fluorescence optical qualitative and quantitative determination methods for the diagnosis of cell properties, in biosensors (point-of-care measurements), exploration of the genome and in miniaturization technology. Typical applications lie in the fields of cytometry, cell sorting, fluorescence correlation spectroscopy (FCS), ultra-high throughput screening (UHTS), multicolor fluorescence in situ hybridization (FISH) and in microarrays (gene and protein chips).

Here, a microarray is a grid-like arrangement of molecules immobilized on at least one surface which can be used for the study of the interaction between receptors and ligands. A grid-like arrangement means more than two molecules which are different from each other and which are immobilized in different, predefined regions of known positions on a surface.

A receptor is a molecule which has an affinity to a given ligand. Receptors can be naturally occurring or artificially produced molecules.

Receptors can be used in their pure state or bound to other species. Receptors can be bound covalently or non-covalently either directly or via certain coupling mediators to a bonding partner.

Examples of receptors which can be detected by means of this invention include agonists and antagonists for cell membrane receptors, toxins and other poisonous substances, viral epitopes, hormones like opiates and steroids, hormone receptors, peptides, enzymes, enzyme substrates, active substances that act as co-factors, lectines, sugars, oligonucleotides, nucleic acids, oligosaccharides, cells, cell fragments, tissue fragments, proteins and antibodies, but they are not limited to the named substances.

A ligand is a molecule that is recognized by a particular receptor. Examples of ligands which can be detected by this invention include agonists and antagonists for cell membrane receptors, toxins and other poisonous substances, viral epitopes, hormones like opiates and steroids, hormone receptors, peptides, enzymes, enzyme substrates, active substances that act as co-factors, lectines, sugars, oligonucleotides, nucleic acids, oligosaccharides, cells, cell fragments, tissue fragments, proteins and antibodies, but they are not limited to the named substances.

The invention is subsequently to be illustrated in more detail by means of embodiment examples and the drawings.

BRIEF DESCRIPTION OF THE DRAWINGS

In the accompanying drawings:

FIG. 1 shows the structural formula of benzopyrylium salt 2a;

FIG. 2 shows the synthesis and structural formula of benzopyrylium salt 2b;

DESCRIPTION OF THE PREFERRED EMBODIMENTS

Embodiment Examples

Figures 1, 2:
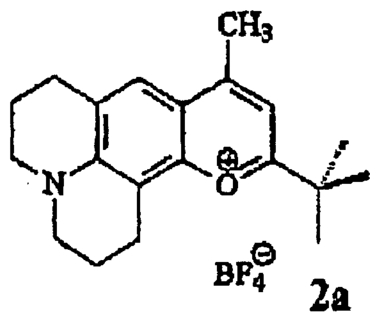

1. Instruction for the Preparation of 11-(2,2-dimethylethyl)-9-methyl-1H,2H,3H,5H,6H,7H-pyrano[2,3-f]pyrido[3,2,1-ij]chinolin-12-ium tetrafluoroborate 2b (BS28), cf. FIG. 2:

50 ml of a 1.0 molar solution of methylmagnesiumbromide in dibutylether are added drop by drop to a cooled solution of 7.3 g (0.0245 mol) 11-(2,2-dimethylethyl)-1H, 2H,3H,5H,6H,7H-pyrano[2,3-f]pyrido[3,2,1-ij]chinolin-9-on in 50 ml ethylenglycol-dimethylether. The mixture was heated to a temperature of 40 degrees C. for a time span of 30 minutes. After cooling down to 0 degrees C., 70 ml of a saturated $NH_4Cl$ solution and diluted hydrochloric acid were added for hydrolysis. The organic phase was separated and extracted using 4×10 ml diethylether. The solvent was removed in a rotary evaporator and the oily residue was dissolved in 20 ml pure acetic acid. The addition of 3 ml $HBF_4$ (48–50%) and the dilution with diethylether created a precipitant which is filtered out and recrystallized from pure acetic acid.

A yield of 3.35 g (35%), melting point 175–180 degrees C.—$^1$H NMR (400 MHz, $CDCl_3$+$CF_3CO_2D$): 1.43 (s, 9H), 1.90 (m, 2H), 2.06 (m, 2H), 2.67 (m, 2H), 2.92 (m, 2H), 3.35 (m, 2H), 3.57 (m, 2H), 3.95 (s, 3H), 6.90 (s, 1H), 7.58 (s, 1H):—$C_{20}H_{26}BF_4NO$ (383.24): calculated C 62.68, H 6.84, N 3.65, found C 63.06, H 6.72, N 3.48.

2. General Instruction for the Preparation of the Non-symmetrical Trimethines OB11, OB14, OB15 and OB20:

0.01 mol of the corresponding 4-methyl-benzopyrylium-tetrafluoroboratee according to formula 2a (BS4) or 2b (BS28) (cf. FIG. 1 and 2) and 0.01 mol methylene-active N-heterocycle were dissolved in 20 ml acetanhydride and after the addition of 2.0 g of triethoxymethane and 5 ml pyridine heated for about 10 minutes. The crude dye product was precipitated with 30 ml of diethylether after the solution had cooled down to room temperature. The precipitate was filtered out and purified by means of column chromatography.

Figure 3:
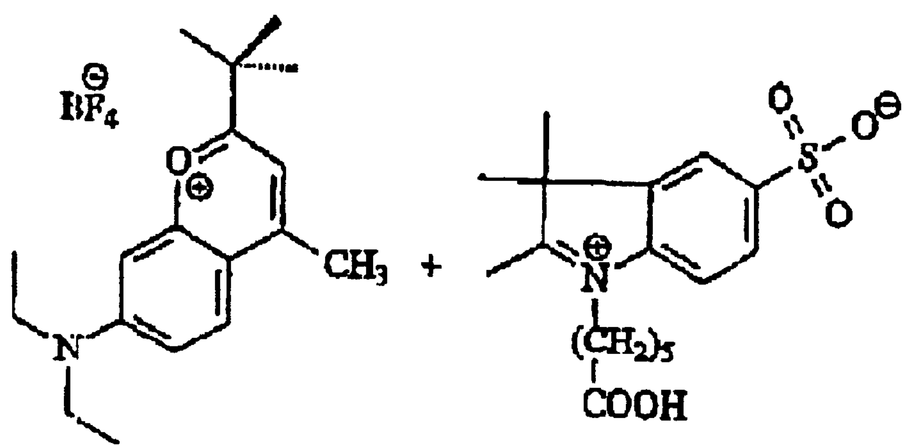
FIG. 3 shows the synthesis and structural formula of trimethine OB11 (DY-630)
Figure 3:
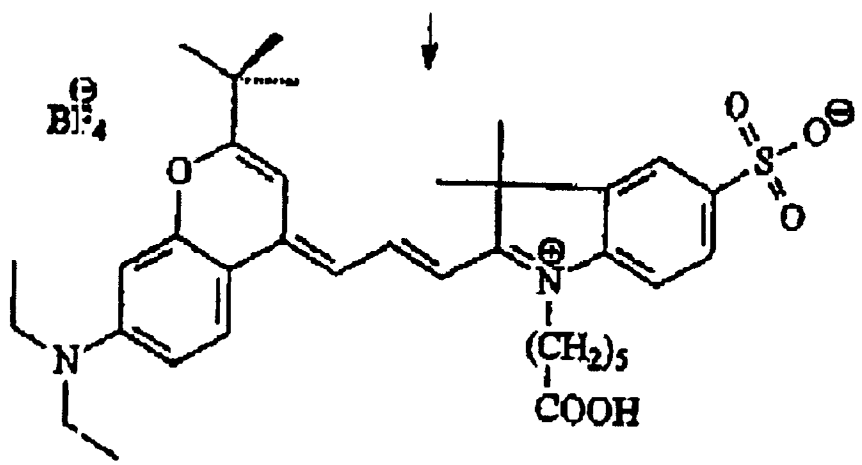

3. 1-(5-carboxypentyl)-3,3-dimethyl-2-[3-(7-N,N-diethylamino-2-(1,1-dimethylethyl)-4H-benzopyran-4-ylidene)-1-propenyl]-3H-indolium-5-sulfonate OB11 (DY-630):

0.01 mol of 2a and 0.01 mol of 1-(5-carboxypentyl)-2,3,3-trimethyl-3H-indolium-5-sulfonate were transformed according to the general specification 1, see FIG. 3. Column chromatography: $SiO_2$, eluent ethanol. Yield of 3.2 g (50%), melting point 280–282 degrees C.—$^1$H NMR (400 MHz, DMSO-d6): 1.10–1.86 (m, 27H), 2.16 (m, 2H), 3.54 (m, 4H), 4.13 (m, 2H), 6.58 (d, 1H), 6.74 (s, 1H), 6.97 (s, 1H), 7.06 (d, 1H), 7.14 (d, 1H), 7.36 (d, 1H), 7.68 (d, 1H), 7.78 (s, 1H), 8.08 (d, 1H), 8.32 (t, 1H)—$^{13}$C NMR (100 MHz, DMSO-d6): 12.30, 21.51, 24.32, 25.66, 26.56, 27.55, 34.07, 36.37, 43.72, 44.22, 48.87, 96,36, 99.40, 104.11, 109.85, 110.28, 112.48, 113.27, 119.66, 126.09, 140.23, 141.81, 145.59, 147.09, 162.14, 172.33, 174.64—MS (FAB in dmba): 657 (M+Na$^+$), 635 (M+H$^+$), 391, 359, 258, 257—$C_{36}H_{46}N_2O_6S$ (634.83): calculated C 68.11, H 7.30, N 4.41, found C 68.25, H7.33, N 4.39.

4. 1-(3-hydroxypropyl)-4-[3-(7-N,N-diethylamino-2-(1,1-dimethylethyl)-4H-benzopyran-4-ylidene)-1-propenyl]-chinolinium-tetrafluoroborate OB 14:

0.01 mol of 2a and 0.01 mol of 1-(3-hydroxypopyl)-4-methylchinolinium-iodide were transformed according to general specification 1. Column chromatography: $SiO_2$, eluent toluol/ethanol 1/1. Yield of 2.4 g (42%), melting point 162–164 degrees C.—$^1$H NMR (400 MHz, $CDCl_3$): 1.17 (t, 6H), 1.32 (s, 9H), 2.14 (m, 2H), 2.25 (s, 1H), 3.39 (q, 4H), 3.71 (m, 2H), 4.89 (m, 2H), 6.31 (d, 1H), 6.56 (s, 1H), 6.62 (m, 2H), 7.01 (d, 1H), 7.60 (t, 1H), 7.67 (d, 1H), 7.77 (d, 1H), 7.84 (t, 1H), 7.93 (d, 1H), 8.12 (t, 1H), 8.31 (d, 1H), 9.27 (d, 1H).—$^{13}$C NMR (100 MHz, $CDCl_3$): 12.52, 28.08, 32.01, 36.20, 44.61, 52.53, 57.52, 97.05, 97.94, 109.58, 109.94, 110.91, 111.77, 113.61, 117.72, 124.79, 125.38, 125.50, 127.13, 133.64, 137.96, 140.92, 142.20, 144.96, 150.87, 151.74, 155.40, 167.12—MS (FAB in dmba): 483 (M$^+$)—$C_{32}H_{39}BF_4N_2O_2$ (570.48): calculated C 67.37, H 6.89, N4.91, found C 67.30, H 6.92, N 4.89.

5. 1-(5-carboxypentyl)-3,3-dimethyl-2-[3-(11-(2,2-dimethylethyl)-1H,2H,3H,5H,6H,7H-pyrano[2,3-f]pyrido[3,2,1-ij]chinoline-9-ylidene)-1-propenyl]-3H-indolium-5-sulfonate OB 15 (DY-635):

0.01 mol of 2b and 0.01 mol of 1-(5-carboxypentyl)-2,3,3-trimethyl-3H-indolium-5-sulfonate were transformed according to the general specification 1.

Column chromatography: $SiO_2$, eluent ethanol. Yield of 2.9 g (44%), melting point >300 degrees C.—$^1$H NMR (250 MHz, DMSO-d6): 1.10–1.56 (m, 19H), 1.91 (m, 4H), 2.08 (m, 4H), 2.83 (m, 4H), 3.38 (m, 4H), 4.03 (m, 2H), 6.45 (d, 1H), 6.97 (s, 1H), 7.13 (d, 1H), 7.26 (d, 1H), 7.62 (d, 1H), 7.73 (s, 1H), 7.78 (s, 1H), 8.23 (t, 1H)—$^{13}$C NMR (62 MHz, DMSO-d6): 19.40, 20.43, 24.86, 25.98, 26.61, 27.16, 27.76, 27.85, 28.94, 35.17, 36.71, 43.40, 48.45, 49.04, 49.63, 99.24, 102.90, 105.09, 109.69, 110.03, 112.96, 119.71, 121.85, 123.50, 139.89, 142.18, 144.84, 145.76, 148.56, 148.86, 151.59, 170.08, 171.37—MS (ESI): 681 (M+Na$^+$), 659 (M+H$^+$), 352—$C_{38}H_{46}N_2O_6S$ (658.12): calculated C 69.27, H 7.34, N 4.25, found C 69.20, H 7.37, N 4.29.

6. 1-(5-carboxypentyl)-4-[3-(7-N,N-diethylamino-2-(1,1-dimethylethyl)-4H-benzo-pyran-4-ylidene)-1-propenyl]-chinolinium-6-sulfonate OB20:

0.01 mol of 2a and 0.01 mol 1-(5-carboxypentyl)-4-methylchinolinium-6-sulfonate were transformed according to general specification 1.

Column chromatography: $SiO_2$, eluent ethanol. Yield of 2.1 g (35%), melting point >300 degrees C.—$C_{35}H_{42}N_2O_6S$ (618.76): calculated C 67.93, H 6.84, N 4.53, found C 67.73, H 6.93, N 4.29.

7. Preparation of the NHS Ester of OB11 (DY-630) with N-hydroxysuccinimide (NHS)/N,N'-dicylcohexylcarbodiimide (DCC)

15 mg OB11 (DY-630), 14 mg DCC and 4 mg NHS were dissolved in 1 ml dry DMF. After this, 1 μl of thriethylamine were added. The reaction mixture was stirred for 24 hours at room temperature and then filtered. The solvent was then drawn off, the residue was washed with ether. This reaction was quantitative.

8. Preparation of the NHS Ester of OB15 (DY-635) with N-hydroxysuccinimide (NHS)/N,N'-dicylcohexylcarbodiimide (DCC)

The process was analogous to example 7. This reaction also was quantitative.

9. Excitation and Emission Spectra of 1-(5-carboxypentyl)-3,3-dimethyl-2-[3-(11-(2,2-dimethylethyl)-1H,2H,3H,5H,6H,7H-pyrano [2,3-f]pyrido[3,2,1-ij]chinoline-9-ylidene)-1-propenyl]-3H-indolium-5-sulfonate OB15 (DY-635)

Figure 4:
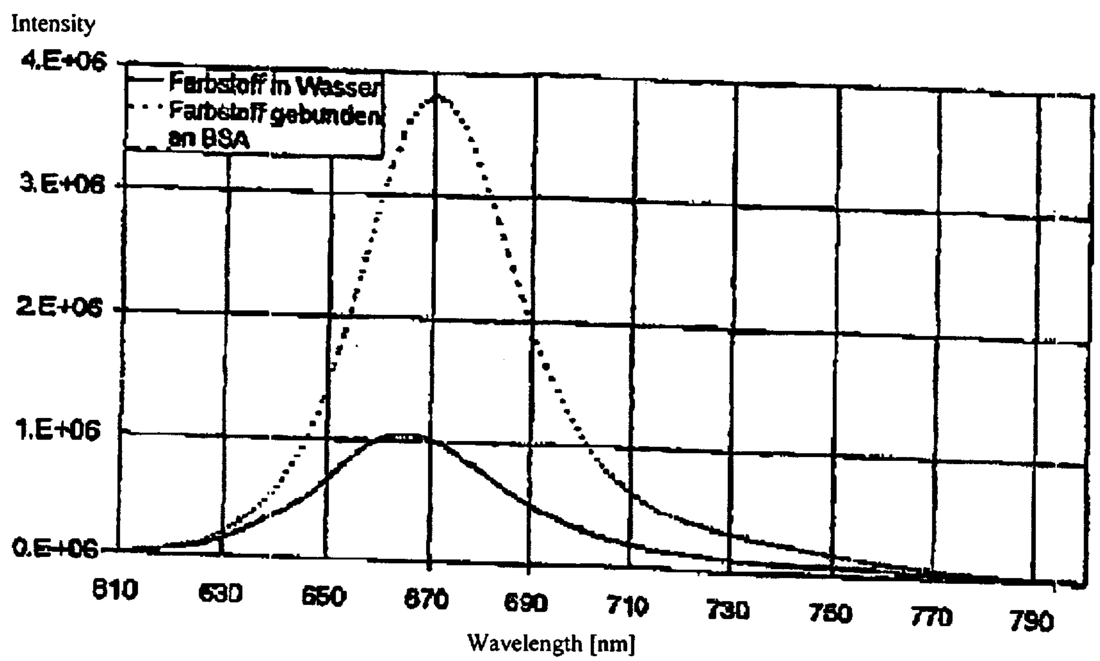
FIG. 4 shows the fluorescent spectra of OB 15 (DY-635) in an aqueous solution and bound to bovine serum albumin (BSA)
Figure 5:
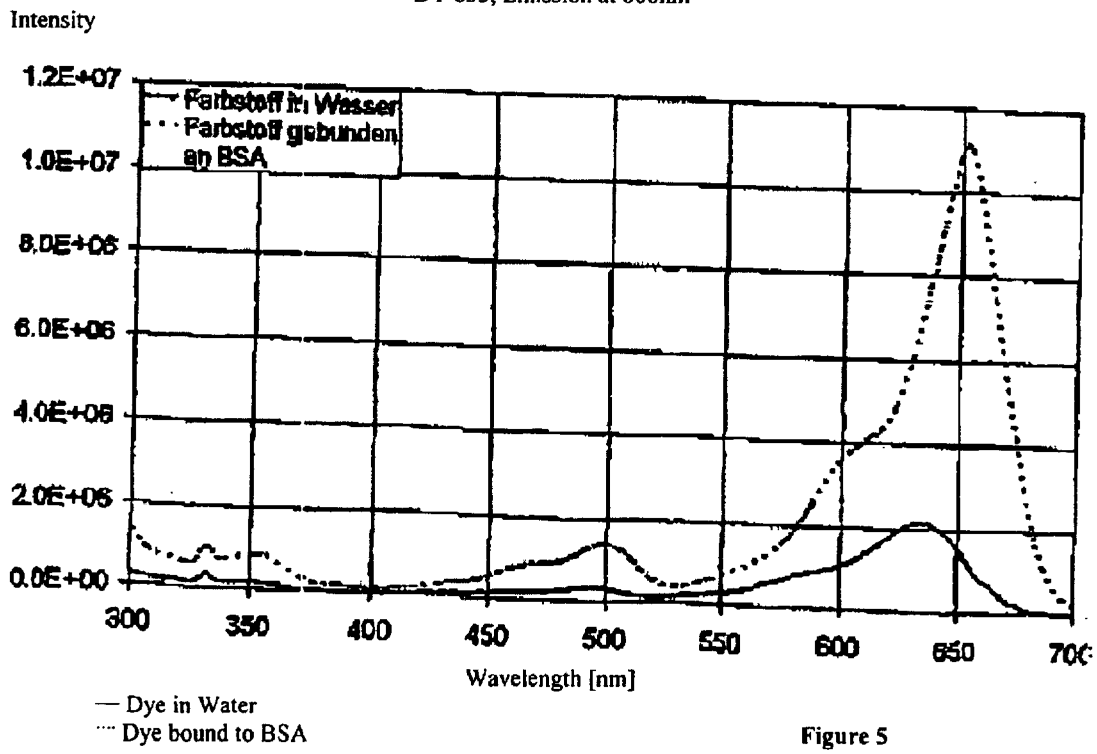
FIG. 5 shows the fluorescent excitation spectra of OB15 (DY-635) in an aqueous solution and bound to bovine serum albumin (BSA).

The diagram in FIG. 4 shows the emissions spectra and the diagram FIG. 5 shows the excitation spectra of 1-(5-carboxypentyl)-3,3-dimethyl-2-[3-(11-(2,2-dimethylethyl)-1H,2H,3H,5H,6H,7H-pyrano[2,3-f]pyrido[3,2,1-ij]chinolin-9-ylidene)-1-propenyl]-3H-indolium-5-sulfonate when in water and when non-covalently bound to bovine serum albumin (BSA), with the more intense spectrum being the one of the BSA conjugate. The concentration of both dye solutions was identical for these measurements.

10. General Specification for the Marking of Proteins

The protein marking was done in a 50 mM bicarbonate buffer (pH 9.0). A parent solution with 0.5 mg reactive dye (for example OB11-NHS-ester, M=732 g*mol$^{-1}$) in 100 μl DMF was created. The protein, for example avidine (M=66000 g*mol$^{-1}$) was dissolved step by step in portions of 1 mg in 200 ml bicarbonate buffer; after this, varying volumes of the different and—if necessary—diluted dye parent solutions were added to the different protein aliquots. The reaction mixtures were then stirred for one to two hours at room temperature. The free dye was separated from the marked proteins by means of gel chromatography (Sephadex G25 medium, eluent PBS pH 7.2 22 mM).

While the foregoing description and drawings represent the present invention, it will be obvious to those skilled in the art that various changes may be made therein without departing from the true spirit and scope of the present invention.

What is claimed is:

1. Laser-compatible NIR marker dyes based on polymethines of the general formula I, II or III

I

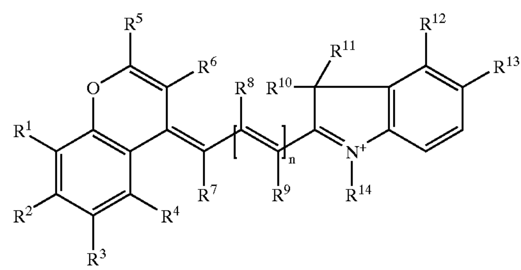

-continued

II

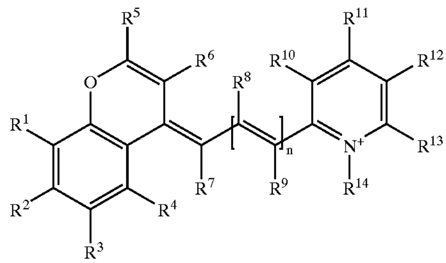

III

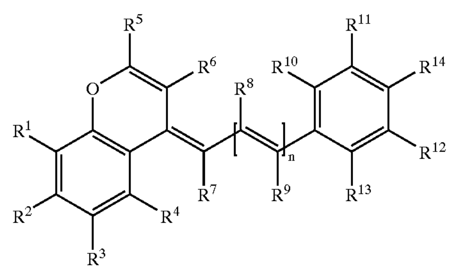

wherein $R^1$ to $R^{14}$ are equal or different and are present in each case hydrogen, chlorine, bromine, an aliphatic or mononuclear aromatic group, each having at most 12 carbon atoms which may contain as a substituted group in addition to carbon and hydrogen, up to 4 oxygen atoms and zero, one or two nitrogen atoms or a sulfur atom or a sulfur and a nitrogen atom or represent an amino function, having a nitrogen atom to which there is bound, hydrogen or at least one substituent having up to 8 carbon atoms, said substituent selected from the group consisting of carbon, hydrogen and up to two sulfonic acid groups.

2. The marker dye of claim 1, wherein at least one of the groups $R^1$ to $R^{14}$ contains a solubilizing or ionizable group.

3. The marker dye of claim 2, wherein said solubilizing or ionizable group is bound via an aliphatic or heteroallphatic group.

4. The marker dye of claim 2, wherein the solubilizing or ionizable group is $SO_{-3}$, $CO_2H$, OH or a combination thereof.

5. The marker dye of claim 1, wherein at least one of the said groups $R^1$ to $R^{14}$ contains a reactive group which is capable of reacting with a biomolecule to form a covalent bond.

6. The marker dye claim 5, wherein the reactive group is a N-hydroxysuccinimide ester group or a maleimide group or a phosphoramidite group.

7. The marker dye of claim 5, wherein any of the groups $R^1$ to $R^{14}$ which is allphatic and contains form 1 to 6 carbon atoms.

8. The marker dye of claim 1, wherein n represents zero, 1 or 2.

* * * * *

UNITED STATES PATENT AND TRADEMARK OFFICE

CERTIFICATE OF CORRECTION

PATENT NO. : 6,750,346 B2
DATED : June 15, 2004
INVENTOR(S) : Peter Czerney et al.

It is certified that error appears in the above-identified patent and that said Letters Patent is hereby corrected as shown below:

Title page,
Item [73], Assignee, should be:
-- Dyomics GmbH
Jena, Germany --.

Signed and Sealed this

Fifteenth Day of November, 2005

JON W. DUDAS
*Director of the United States Patent and Trademark Office*